United States Patent [19]

Lang et al.

[11] Patent Number: 4,954,619
[45] Date of Patent: Sep. 4, 1990

[54] O-BENZYL-N-HYDROXYALKYL DERIVATIVES OF CHITOSAN AND NAIL POLISH CONTAINING THE SAME

[75] Inventors: Günther Lang, Reinheim; Gerhard Maresch; Hans-Rudi Lenz, both of Darmstadt, all ofr, Fed. Rep. of Germany

[73] Assignee: Wella Aktiengesellschaft, Darmstadt, Fed. Rep. of Germany

[21] Appl. No.: 217,763

[22] Filed: Jul. 11, 1988

[30] Foreign Application Priority Data

Jul. 18, 1987 [DE] Fed. Rep. of Germany ....... 3723811

[51] Int. Cl.$^5$ .................. C08B 37/00; A61K 7/00
[52] U.S. Cl. ............................. 536/20; 424/61
[58] Field of Search .............. 536/20; 514/55; 424/61

[56] References Cited

U.S. PATENT DOCUMENTS

| | | | |
|---|---|---|---|
| 3,953,608 | 4/1976 | Vanlerberghue et al. | 536/20 |
| 4,195,175 | 3/1980 | Peniston et al. | 536/20 |
| 4,424,346 | 1/1984 | Hall et al. | 536/20 |
| 4,528,283 | 7/1985 | Lang et al. | 536/20 |
| 4,772,689 | 9/1988 | Lang et al. | 514/55 |
| 4,772,690 | 9/1988 | Lang et al. | 514/55 |

FOREIGN PATENT DOCUMENTS

| | | |
|---|---|---|
| 0085370 | 10/1983 | European Pat. Off. . |
| 3112888 | 2/1982 | Fed. Rep. of Germany . |
| 3205545 | 10/1982 | Fed. Rep. of Germany . |
| 3537333 | 4/1988 | Fed. Rep. of Germany . |

Primary Examiner—Ronald W. Griffin
Assistant Examiner—Everett White
Attorney, Agent, or Firm—Michael J. Striker

[57] ABSTRACT

Nail polish is disclosed, based upon a film-former, a resin component and a solvent system, containing as film-former and/or resin component an O-benzyl-N-hydroxyalkyl chitosan fo the formula (I)

$$HO[C_6H_{11-m-q}NO_4(R^1)_m(R^2)_n(R^3)_q]_pH \qquad (I)$$

(with m=0 to 0.6; n=0.1 to 10; q=0.1 to 4; p=an integer from 50 to 5,000; R$^1$=acetyl; R$^2$=hydroxyethyl, 2-hydroxypropyl or 2-hydroxybutyl and R$^3$=benzyl).

The polish film obtained with the nail polish possesses a high luster, outstanding adhesion, as well as an increased hardness compared to nail polishes based upon nitro-cellulose, with even more sufficient elasticity. Also included in the present invention are the new O-benzyl-N-hydroxyalkyl-chitosans of formula (I).

15 Claims, No Drawings

O-BENZYL-N-HYDROXYALKYL DERIVATIVES OF CHITOSAN AND NAIL POLISH CONTAINING THE SAME

BACKGROUND OF THE INVENTION

The invention concerns new O-benzyl-N-hydroxyalkyl derivatives of chitosan, as well as nail polish containing these compounds.

The essential characteristics which should distinguish a good nail polish are sufficient hardness, good applicability (ease of application), short drying period, high storage stability (i.e. the nail polish should maintain its homogeneity and a good stability over a long time period), resistance against light, water, washing agents and rinsing agents, as well as, above all, harmlessness to skin and nails. Finally, the nail polish should provide a polish film with satisfactory characteristics. The characteristics expected of such a nail polish film are uniform thickness, high luster, prerequisite for which is a smooth surface, outstanding adhesiveness to the keratin of the nails, and a good elasticity. Good elasticity avoids breaks in the polish and also avoids its peeling off.

Nail polish contains, in general, a film-former, a resin component and a solvent system, as well as, if necessary, softeners, pigments and customary additives.

Typically, nail polishes contain nitro-cellulose as film-former. Particularly preferred herewith are ester-soluble nitro-celluloses (so-called E-collodium wool or "RS"-nitro-cellulose) with moderate to low viscosity. Nail polish based upon nitro-cellulose possesses, however, a number of disadvantages: thus, for example, with the use of nitro-cellulose, discolorations of the nail polish occur in the course of time. Moreover, nitro-cellulose tends to display sudden changes in viscosity, which makes more difficult a uniform application of the nail polish. In addition, it must be noted that the nitro-cellulose employed in nail polishes is neutral, i.e. free of acid components. A content of free acid can lead, namely, to not only an injury to the finger nails and the skin, but also to decomposition of the dyes contained in the nail polish.

It is also known that nitro-cellulose, on account of its high degree of inflammability and explosiveness, must be manufactured and handled with the greatest care.

In order to obtain satisfactory results with regard to adhesiveness, luster and hardness of the nail polish, the modern combination polishes based upon nitro-cellulose must be supplemented with various other resin components. Coming into consideration in this connection are, in addition to natural polymers such as e.g. shellac, elemi gum and, particularly, colophonium, synthetic resins, such as for example, polystyrene, polyvinyl acetate and polymethacrylic acid ester, e.g. polypropyl methacrylate and polymethyl methacrylate. Moreover, alkyde resins, such as e.g. polymerizates of phthalic acid anhydride and glycerin, as well as formaldehyde/urea-resins and, preferably, arylsulfonamide/-rormaldehyde-resins, such as e.g. a polymer produced from equimolar amounts of formaldehyde and p-toluene sulfonamide, which is known by the designation Santolite$^R$, are employed.

It has been proven many times that one can avoid the above-mentioned disadvantages through the use of synthetic copolymers, such as e.g. copolymerizates of hydrophobic and hydrophilic monomer units (see, e.g. EP-OS No. 00 85 370), instead of nitro-cellulose as film-former in nail polishes. Moreover, reference is made to the German Offenlegungsschriften DE-OS No. 31 12 888 and DE-OS No. 32 05 545.

Despite all of the previous difficulties in producing a nitro-cellulose-free nail polish, and whether or not a nail polish film based exclusively on nitro-cellulose cannot satisfy the mentioned requirements and are first made more hard, more adhesive, more elastic and more resistant by means of addition of further resin components, these film-formers represent, now as berore, unavoidable components of many nail polishes. It has not been possible, namely, to develop nitro-cellulose-free nail polishes which provide, in all of the characteristics essential for nail polish, equally good or indeed better results than nail polish based upon nitro-cellulose. Thus, for example, with the above mentioned nail polishes based upon synthetic polymers, problems can arise on account of the physiological effect of possible present traces of monomer, which are removable from the polymerizate only with great difficulty.

In contrast hereto, the chitin alkyl ester suggested for use as film-former in nail polishes in DE-OS No. 35 37 333 is physiologically urobjectionable. However, this chitin alkyl estercan only be obtained by means of a complicated and expensive process. In particular, the production of high molecular, sufficiently substituted chitin alkyl esters, which can also form closed film surfaces without addition of softeners, is only possible under considerable technical expenditure and precise reaction conditions at 0° C.

SUMMARY OF THE INVENTION

It is therefore an object of the present invention to make available physiologically compatible, nitro-cellulosefree nail polish, which provides an equally good or better polish film than nail polish based upon nitro-cellulose, and the film-forming components of which are obtainable by means of a technically simple and economical synthesis.

It has now, surprisingly, been discovered, that with use of certain O-benzyl-N-hydroxyalkyl derivatives of chitosan, soluble in organic solvents, as film-former instead of nitro-cellulose, equally good quality or even better polish films can be obtained. The polish films obtained with nail polish based upon these O-benzyl-N-hydroxyalkyl chitosans distinguish by their high luster, outstanding adhesiveness and increased hardness compared to nitro-cellulose-based nail polishes, with more sufficient elasticity.

It has further been discovered that it is possible to advantageously replace the resin components additionally contained in nitro-cellulose-based nail polishes by means of the O-benzyl-N-hydroxyalkyl chitosans according to the present invention. Herewith are avoided the disadvantages that can occur upon use of arylsulfonamide/formaldehyde-resins, for example (such as e.g. poor light resistance of the nail polish, release of formaldehyde or increased risk of allergic reactions).

The present invention concerns a nail polish based upon a film-former, a resin component and a solvent system, characterized by a content as film-former and/or resin component of O-benzyl-N-hydroxyalkyl chitosan of the formula (I)

$$HO[C_6H_{11-m-q}NO_4(R^1)_m(R^2)_n(R^3)_q]_pH \qquad (I),$$

wherein
m is any optional numerical value from 0. to 0.6, n is any optional numerical value from 0.1 to 10,
q is any optional numerical value from 0.1 to 4,
the degree of polymerization p is an integer from 50 to 5,000, $R^1$ is the group

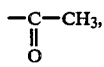

$R^2$ is the group

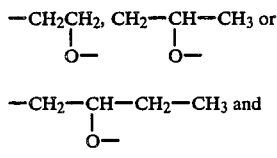

$R^3$ is the group

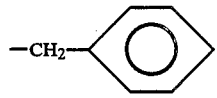

The O-benzyl-N-hydroxyalkyl chitosans contained in the nail polish according to the present invention preferably possess an average molecular weight from about 5,000 to 1,800,000. Particularly preferred is an average molecular weight from about 10,000 to 500,000, which is determined by means of molecular exclusion chromatography in ultrastyragel columns from the company WATERS, using tetrahydrofuran as eluent.

The limit viscosity numbers of the O-benzyl-N-hydroxyalkyl chitosans of formula (I), determined with a DIN-Ubbelohde-Viscosimeter at 25° C. in tetrahydrofuran, lie within a range from about 5 to 200 ml/g, preferably from 10 to 120 ml/g.

The degree of benzyl substitution of the O-benzyl-N-hydroxyalkyl chitosans, determined from $^1$H-NMR-spectra, amounts to preferably from 0.8 to 3.8.

The O-benzyl-N-hydroxyalkyl chitosans of formula (I) employed as film-former and/or resin component in the nail polish according to the present invention, lead neither to skin irritations, nor are they toxic; they are physiologically harmless and bio-degradable.

The O-benzyl-N-hydroxyalkyl chitosans of formula (I) can, indeed depending upon use as film-former or resin component in the nail polish, be employed alone or together with other resins, such as for example, nitrocellulose.

When employed as film-former, the O-benzyl-N-hydroxyalkyl chitosans of formula (I) should be employed in a concentration of about 3 to 30% by weight. An addition of further resin components, as is necessary with the employment of nitro-cellulose as film-former, is not required herewith.

When the O-benzyl-N-hydroxyalkyl chitosans of formula (I) are employed as resin component, they are contained in the nail polish according to the present invention in a concentration from about 10 to 70% by weight, relative to the amount of the contained film-formers, or in a concentration from about 1 to 21% by weight, relative to the total weight of the nail polish.

The nail polish according to the present invention provides, upon suitable formulation, even without addition of softeners, a highly lustrous, smooth, transparent, adhesive film. However, in determined cases, one or more softeners can advantageously be added to the nail polish in a total amount from about 0.2 to 12% by weight, in order to confer to the polish film an increased flexibility and elasticity, so as to decrease its tendency to shrinkage, as well as to improve its adhesiveness on the nail plate and its luster. The employed softeners should be high-boiling, i.e. non-volatile, miscible with the film-former and other components of the nail polish, colorless, odorless, as well as non-toxic. Of use are esters of polybasic acids, such as for example, dibutylphthalate, diisobutylphthalate, diamylphthalate, dioctylphthalate, dimethoxyethylphthalate, tributylphosphate, triphenylphosphate, tricresylphosphate, tributoxyethylphosphate, triethylcitrate, tributylcitrate, tributylacetylcitrate and dibutyltartrate, esters of saturated and unsaturated fatty acids, such as e.g. butyl stearate, butylacetylricinoleate and glycerylacetylricinoleate, castor oil, camphor as well as mixtures of these compounds.

The nail polish according to the present invention contains a solvent system in a concentration from about 60 to 80% by weight.

The designation "solvent system" means a mixture of low-, medium- and high-boiling organic solvents, which make possible a good stretchability and relatively short drying time for the polish film.

Coming into consideration as low-boiling solvents are those having a boiling point from about 30° to 100° C., such as e.g. ethanol, isopropanol, acetone, methylene chloride, ethyl acetate and methyl acetate. Examples of medium-boiling solvents which have a boiling point from about 100° to 150° C. are butanol, amyl alcohol, toluene, ethylene glycol monomethylether, butyl acetate and amyl acetate. The high-boiling solvents have a boiling point from about 150° to 200° C., such as e.g. dichloroethylether, diethylene glycol monoethylether, diethylene glycol monomethylether, and ethylene glycol.

The nail polish according to the invention can also be provided with color. It contains, in that case, at least one organic or inorganic pigment, preferably in an amount from about 0.1 to 6% by weight. As organic pigments, mention may be made by way of example of calcium-, aluminum- and lithol-dye polishes, such as e.g. the aluminum polishes of FD & C Yellow No. 5 (C.I. 19 140:1), the aluminum polishes of FD & C Yellow No. 6 (C.I. 15 885:1), Lithol Rubin B (C.I. 15 850) and the Lithol polishes D & C Red Nos. 10, 11, 12 and 13 (C.I. 15 630), as well as Guanine (C.I. 75 170). Additional dye polishes useful in the nail polish according to the invention such as e.g. the aluminum polishes of D & C Red No. 7, the calcium polish of D & C Red No. 7 and the calcium polish of D & C Red No. 34, are described in CTFA Cosmetic Ingredient Dictionary (1982), The Cosmetic, Toiletry and Fragrance Association, Inc., Washington, D.C.

Examples of useful inorganic pigments include brown and red iron oxide, titanium dioxide and bismuth oxide chloride.

The nail polish according to the present invention can contain, in addition, all of the components customary for a nail polish, such as for example, perfume oils or additives which retard sedimentation. Sedimentation-retardants include in particular, silicon dioxide-containing compounds, such as e.g. colloidal silicic acid or Montmorillonite-type clays (e.g. Bentone 27 and Bentone 38 of National Lead Co.), as well as metal soaps, such as e.g. aluminum- and zinc stearate The new O-benzyl-N-hydroxyalkyl chitosans of formula (I) contained in the present nail polishes are physiologically harmless and biodegradable. In addition to use in nail polish, the new O-benzyl-N-hydroxyalkyl chitosans are also useful in glues and varnishes, in pharmaceuticals and cosmetics, as well as in the production of foils and films.

Another object of the present invention therefor are new macrorolecular O-benzyl-N-hydroxyalkyl compounds derived from chitosan, of the formula (I)

wherein
m is any numerical value from 0 to 0.6,
n is any numerical value from 0.1 to 10 and
q is any numerical value from 0.1 to 4,
p is an integer from 50 to 5,000,
$R^1$ is

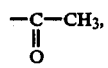

$R^2$ is

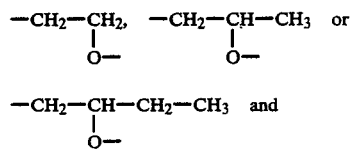

$R^3$ is

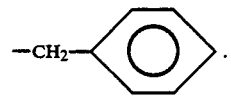

The new O-benzyl-N-hydroxyalkyl chitosans of formula (I) are obtained by reacting chitosan, either in a two-stage reaction, initially with an epoxide and then with benzyl chloride, or simultaneously with both these alkylation agents, however at two different reaction temperatures, so as to allow the chitosan to penetrate.

With the two-stage process for the production of the compounds of formula (I) one reacts chitosan, composed of chitin, deacetylated to the extent of 40 to 96%, in a first reaction stage in the presence of a suitable dispersing agent at a temperature from 20° to 120° C., preferably 80° to 100 ° C., for 6 to 60 hours with a $C_2$-$C_4$-epoxide (ethylene oxide, propylene oxide, butylene oxide), and then the obtained N-hydroxyalkyl chitosan is reacted in a second reaction stage, with benzyl chloride, in alkaline medium, at 40° to 120° C., preferably from 60° to 90° C., for 6 to 60 hours.

With the simultaneous reaction of the chitosan with both alkylation agents (i.e. epoxide and benzyl chloride), the reaction mixture is initially stirred for 6 to 60 hours at 20° to 120° C., preferably 20° to 40° C., in an autoclave. Under these reaction conditions, there occurs predominantly an N-hydroxyalkylation of the chitosan. Thereafter, the reaction mixture is further stirred after being adjusted to an alkaline pH-value, at 40° to 120° C., preferably 60° to 90° C., for 6 to 60 hours. This results in the O-alkylation of the N-hydroxyalkyl chitosan.

The molar ratio of chitosan and alkylation agent is selected in each case to be from 1:3 to 1:5.

At low reaction temperatures, the compounds employed as alkylation agents also serve as dispersing agent. At higher temperatures, organic solvents, such as e.g. isopropanol, tert.butanol, ethylene glycol dimethylether, dioxan and toluene are employed as dispersing agents.

The working-up of the obtained reaction mixture follows in such manner that after removal of the excess epoxide, the hydroxyalkylated intermediate product is isolated from the organic solvent by compressing, or after the O-benzylation, in alkaline medium, the reaction mixture is initially neutralized, then concentrated, and the inorganic salts separated by means of decanting, centrifugation or filtration. Subsequently, the chitosan derivative is precipitated in acetone or petroleum ether for the removal of glycols or glycolethers, and finely dispersed. Then, the chitosan derivative is filtered off and dried.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Production Examples

EXAMPLE 1

PRODUCTION OF O-BENZYL-N-HYDROXYPROPYL CHITOSAN (TWO-STAGE PROCESS)

(A) N-hydroxypropylation of chitosan 50 g (0.31 mol) low-molecular chitosan are dispersed in a mixture of 100 ml ethanol or isopropanol and 100 ml water, and reacted in an autoclave at 100° C. with 104.5 g (1.8 mol) of propylene oxide, for 6 hours.

After the conclusion of the reaction, the reaction mixture, upon after-rinsing with about 1 liter ethanol/water (1:1) or isopropanol/water (1:1) is introduced from the pressure reactor into a flask and concentrated n a vacuum to a volume of about 150 to 200 ml. Subsequently, the N-hydroxypropyl chitosan is precipitated in an 8 to 10-fold amount of acetone.

In order to remove any enveloped propylene glycol, the precipitated derivative is then finely dispersed by means of a high-speed stirrer. The finely flocculent sediment is then separated across a G3-glass-sinter suction filter and washed with acetone until the filtrate is colorless.

After drying in a vacuum drying cabinet at 50° C., one obtains 68 g of water-soluble N-hydroxypropyl chitosan. Characteristic data:

| | |
|---|---|
| Limit viscosity number (Eta): | 80 ml/g |
| Degree of substitution of hydroxypropyl: | 1.4 to 1.6 |
| Pendulum hardness: | 204 sec. |
| Water vapor absorption: | 8% |

(B) O-benzylation of N-hydroxypropyl chitosan 50 g (0.21 mol) N-hydroxypropyl chitosan from Example 1A, 20.2 ml (0.32 mol) of 43% caustic soda, as well as 235 ml toluene are reacted in an autoclave with 53.16 g (0.48 mol) of benzyl chloride for 24 hours at 90° C.

After termination of the reaction, the reaction mixture is diluted with water, the pH is adjusted to 7, and then it is concentrated in a vacuum until dry.

The reaction product is dissolved in acetone. Then, it is decanted from precipitated salts, and the obtained acetonic solution is clarified by means of centrifugation and decanting. The solution is then concentrated in a vacuum to a volume of about 100 ml, and the chitosan derivative is precipitated by addition of water. The chitosan derivative is dried in a vacuum at 50° C. The so-obtained product is extracted in petroleum ether for removal of the residual benzyl alcohol. After evacuation in a vacuum across a glass-sinter suction funnel and renewed drying at 50° C. in a vacuum, 67 g of O-benzyl-N-hydroxypropyl chitosan, soluble in organic solvent are obtained.

Characteristic data:

| | |
|---|---|
| Limit viscosity number (eta): | 27 ml/g |
| Degree of substitution of benzyl: | 2.2 |
| Degree of substitution of hydroxypropyl: | 1.7 |
| Pendulum hardness: | 173 sec. |
| Water vapor absorption: | 1.6% |

EXAMPLE 2

Production of O-benzyl-N-hydroxyethyl Chitosan ("One Pot" Process)

50 g (0.31 mol) of low-molecular chitosan are dispersed in a mixture composed of 180 ml ethylene glycol dimethylether and 20 ml distilled water, and brought to reaction in an autoclave with a total of 79.3 g (1.8 mol)=90 ml ethylene oxide at 40° C. The addition of ethylene oxide follows portionwise (in each case 30 ml after the resulting pressure drop) over a time period of about 2 hours.

Subsequently, the reaction mixture is stirred at 40° C. for 6 hours, and then the excess epoxide is removed from the solution by means of inert gas. The reaction mixture is reacted with 118.0 g (1.27 mol) of 43% caustic soda, 235.4 g (1.86 mol) =214 ml benzyl chloride as well as 200 ml ethylene glycol dimethylether and stirred at 90° C. for 12 hours.

The working-up of the organo-soluble chitosan derivative follows in the same manner as described in Example 1. The yield of O-benzyl-N-hydroxyethyl chitosan amounts to 84 g.

Characteristic data:

| | |
|---|---|
| Limit viscosity number (Eta): | 22 ml/g |
| Degree of substitution of benzyl: | 3.5 |
| Pendulum hardness: | 180 sec. |
| Water vapor absorption: | 1.2% |

EXAMPLE 3

Production of High-Molecular O-Benzyl-N-Hydroxypropyl Chitosan (Two Stage)

(A) N-Hydroxypropylation of Chitosan 50 g (0.31 mol) high-molecular chitosan are dispersed in a mixture of 100 ml ethanol or isopropanol and 100 ml water and reacted in an autoclave at 100° C. with 104.5 g (1.8 mol) propylene oxide for 6 hours.

After conclusion of the reaction, the reaction mixture is introduced from the pressure reactor into a flask, under after-rinsing with about 1 liter ethanol/water (1:1) or isopropanol/water (1:1), and concentrated in a vacuum to a volume of about 150 to 200 ml. Thereafter, the N-hydroxypropyl chitosan is precipitated in the 8 to 10-fold amount of acetone.

In order to remove any enveloped propylene glycol, the precipitated derivative is then finely dispersed by means of a high-speed stirrer. The finely flocculent sediment is then filtered off and washed with acetone until the filtrate is colorless.

After drying in a vacuum at 50° C., 71 g of water-soluble N-hydroxypropyl chitosan are obtained.

Characteristic data:

| | |
|---|---|
| Limit viscosity number: | 990 ml/g |
| Degree of substitution of hydroxypropyl: | 2.0 |
| Pendulum hardness: | 180 sec. |
| Water vapor absorption: | 5.4% |

(B) O-benzylation of N-hydroxypropyl chitosan 50 g (0.21 mol) N-hydroxypropyl chitosan from Example 3A, 20.2 m (0.32 mol) 43% caustic soda as well as 235 ml toluene are reacted in an autoclave with 53.16 g (0.16 mol) benzyl chloride at 90° C. for 24 hours.

After conclusion of the reaction, the mixture is diluted with water, pH-adjusted to 7, and concentrated to dryness.

The reaction product is dissolved in acetone. Subsequently, it is decanted from deposited salt, and the obtained acetonic solution is clarified by means of centrifugation and decanting. The solution is then compressed in a vacuum to a volume of about 100 ml and the chitosan derivative is precipitated by means of addition of water. The chitosan derivative is dried in a vacuum at 50° C. The so-obtained product extracted with petroleum ether for elimination of the residual benzyl alcohol.

After evacuation in a vacuum across a glass-sinter vacuum funnel and renewed drying in a vacuum at 50° C., 73 g of O-benzyl-N-hydroxypropyl chitosan are obtained.

Characteristic data:

| | |
|---|---|
| Limit viscosity number: | 600 to 650 ml/g |
| Degree of substitution of benzyl: | 1.8 to 2.0 |
| Degree of substitution of hydroxypropyl: | 1.0 to 1.2 |
| Pendulum hardness: | 162 to 170 sec. |
| Water vapor absorption: | 1.2 to 1.4% |

Employed as low-molecular chitosan in the Examples is a milled chitosan having a limit viscosity number (Eta) of 160 ml/g and a degree of deacetylation of 90%. The employed high-molecular chitosan has a limit viscosity number (Eta) of 1600 ml/g and a degree of deacetylation of 76%.

The degree of substitution for the hydroxypropyl group and the benzyl group are determined with the aid of a $^1$H-NMR-spectroscope.

The measurement of the limit viscosity numbers (Eta) is performed in an aqueous solution of 0.2 mol/l acetic acid and 0.1 mol/l sodium acetate (chitosan) or in an aqueous solution of 0.2 mol/l acetic acid and 0.1 mol/l sodium chloride (N-hydroxyalkyl chitosan) or in tetrahydrofuran (benzylhydroxyalkyl chitosan) at 25° C. using a DIN-Ubbelohde-Kapillarviskosimeter.

The pendulum hardness is determined by the König method (W. König, "Härtemessungen mit dem Pendelhärteprüfer", Farbe und Lacke 65, pages 435 to 443 (1959); DIN 53 157).

The water vapor absorption is determined at 70% relative humidity compared to 30% relative humidity.

Examples of Nail Polishes

EXAMPLE 4

Colorless Nail Polish

| | |
|---|---|
| 15.0 g | O-benzyl-N-hydroxyethyl chitosan according to Example 2 (Degree of substitution of benzyl = 3.5; limit viscosity no. (Eta) = 22 ml/g) |
| 33.0 g | methylene chloride |
| 28.0 g | ethylene glycol monoethylether |
| 17.0 g | ethanol |
| 5.0 g | dibutylphthalate |
| 2.0 g | diethylene glycol monomethylether |
| 100.0 g | |

EXAMPLE 5

Colored Nail Polish

| | |
|---|---|
| 12.0 g | O-benzyl-N-hydroxyethyl chitosan according to Example 2 (degree of substitution of benzyl = 3.5; limit viscosity no. (Eta) = 22 ml/g) |
| 28.0 g | methylene chloride |
| 20.0 g | ethylene glycol monomethylether |
| 14.5 g | ethanol |
| 9.0 g | ethyl acetate |
| 6.0 g | butyl acetate |
| 4.0 g | dibutyl phthalate |
| 2.0 g | diethylene glycol monomethylether |
| 2.0 g | tricresyl phosphate |
| 2.5 g | pigment |
| 100.0 g | |

EXAMPLE 6

Colorless Nail Polish

| | |
|---|---|
| 6.0 g | O-benzyl-N-hydroxypropyl chitosan according to Example 1 (degree of benzyl substitution = 2.2; limit viscosity no. (Eta) = 27 ml/g) |
| 40.0 g | butyl acetate |
| 30.0 g | ethyl acetate |
| 18.0 g | nitro-cellulose (alcohol moist 65:35) |
| 4.0 g | dibutyl phthalate |
| 2.0 g | camphor |
| 100.0 g | |

EXAMPLE 7

Colored Nail Polish

| | |
|---|---|
| 8.0 g | O-benzyl-N-hydroxypropyl chitosan, Example 1 (degree of benzyl substitution = 2.2; limit viscosity no. (Eta) = 27 ml/g) |
| 35.0 g | ethylene glycol monomethylether |
| 21.5 g | methylene chloride |
| 15.0 g | acetone |
| 12.0 g | nitro-cellulose (alcohol moist 65:35) |
| 6.0 g | dibutyl phthalate |
| 1.5 g | pigment |
| 1.0 g | sedimentation retardant |
| 100.0 g | |

EXAMPLE 8

Colorless Nail Polish

| | |
|---|---|
| 12.0 g | O-benzyl-N-hydroxypropyl chitosan, acc. Ex. 2 (degree of benzyl substitution = 1.8 to 2.0; limit viscosity no. (Eta) = 600 to 650 ml/g) |
| 41.0 g | methylene chloride |
| 15.0 g | ethylene glycol monomethylether |
| 15.0 g | butyl acetate |
| 12.0 g | ethyl acetate |
| 5.0 g | diethylene glycol monomethylether |
| 100.0 g | |

As nitro-cellulose, an ester-soluble nitro-cellulose is employed in these examples, its viscosity in acetone (5% by weight water content), at a content of 22% by weight nitro-cellulose amounting to 400±25 mPas. Determination of the viscosity follows according to German Industrial Norm DIN 53 179, at a temperature of 20°±0.05° C., with a falling sphere viscosimeter according to Höppler (thermostatizable drop tube with a diameter of 15.94 mm; slope of the drop tube relative to vertical: 10°±0.1°; length of measurement stretch: 100 mm) using Sphere No. 4 (material: nickel-iron; diameter: 15.2±0.1 mm; K=0.7 mPas.cm$^3$). Examples of such a nitro-cellulose are "Walsroder Collodiumwolle E 560" from Wolff Walsrode AG, Walsrode and "Nitrocellulose RS ½ Second" from Hercules, Inc., Wilmington, Delaware.

All percentages set forth in this specification are percents by weight.

It will be understood that each of the elements described above, or two or more together, may also find a useful application in other types of compositions differing from the types described above.

While the invention has been illustrated and described as embodied in O-benzyl-N-hydroxyalkyl derivatives of chitosan and nail polish containing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Nail polish based upon a film-former, a resin component and a solvent system, comprising as film-former or resin component an O-benzyl-N-hydroxyalkyl-chitosan of the formula (I)

 (I), wherein
m is any numerical value from 0 to 0.6,
n is any numerical value from 0.1 to 10 and
q is any numerical value from 0.1 to 4,
p is an integer from 50 to 5,000,
$R^1$ is

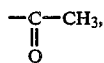

$R^2$ is

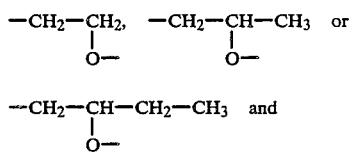

$R^3$ is

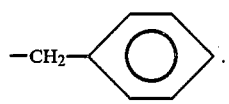.

2. The nail polish according to claim 1, wherein said O-benzyl-N-hydroxyalkyl chitosan of formula (I) displays an average molecular weight from 5,000 to 1,800,000.

3. The nail polish according to claim 2, wherein said average molecular weight is from 10,000 to 500,000.

4. The nail polish according to claim 1, wherein said O-benzyl-N-hydroxyalkyl chitosan of formula (I) displays a limit viscosity number in tetrahydrofuran at 25° C. in the range from 5 to 200 ml/g.

5. The nail polish according to claim 4, wherein said limit viscosity number is from 10 to 120 ml/g.

6. The nail polish according to claim 1, wherein said O-benzyl-N-hydroxyalkyl chitosan of formula (I) displays a degree of benzyl substitution from 0.8 to 3.8.

7. The nail polish according to claim 1, containing said O-benzyl-N-hydroxyalkyl chitosan of formula (I) in a concentration from 3 to 30% by weight.

8. The nail polish according to claim 1, wherein said solvent system is composed of a mixture of low-, medium- and high-boiling organic solvents.

9. The nail polish according to claim 1, wherein said solvent system amounts to 60 to 80% by weight of the nail polish.

10. The nail polish according to claim 1, further comprising at least one organic or inorganic pigment, in an amount from 0.1 to 6% by weight.

11. The nail polish according to claim 1, further comprising a sedimentation-retarding substance.

12. An O-benzyl-N-hydroxyalkyl chitosan of the formula (I)

 (I), wherein
m is any numerical value from 0 to 0.6,
n is any numerical value from 0.1 to 10 and
q is any numerical value from 0.1 to 4,
p is an integer from 50 to 5,000,
$R^1$ is

$R^2$ is

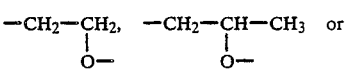

$R^3$ is

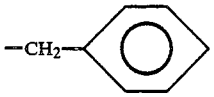.

13. A nail polish containing at least one solvent and from about 3 to 30% by weight of an O-benzyl-N-hydroxyalkyl chitosan of the formula (I):

wherein
m is from 0 to 0.6,
n is from 0.1 to 10,
q is from 0.1 to 4, and
p is an integer such that said O-benzyl-N-hydroxyalkyl chitosan has an average molecular weight of from 10,000 to 500,000, and wherein $R^1$ is

$R^2$ is selected from the group consisting of

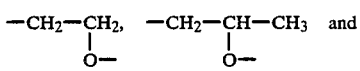

$R^3$ is

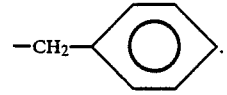.

14. A nail polish according to claim 13 wherein said solvent is a mixture of low, medium and high boiling organic solvents.

15. A nail polish according to claim 14 wherein said solvent mixture includes methylene chloride, ethylene glycol monomethylether and diethylene glycol monomethylether.

* * * * *